(12) United States Patent
Liu et al.

(10) Patent No.: US 8,036,836 B2
(45) Date of Patent: Oct. 11, 2011

(54) DYNAMIC ENVIRONMENTAL CHANGE COMPENSATION OF SENSOR DATA IN STRUCTURAL HEALTH MONITORING SYSTEMS

(75) Inventors: Bao Liu, Cupertino, CA (US); Shawn J. Beard, Livermore, CA (US); Fu-Kuo Chang, Stanford, CA (US)

(73) Assignee: Acellent Technologies, Inc., Sunnyvale, CA (US)

( * ) Notice: Subject to any disclaimer, the term of this patent is extended or adjusted under 35 U.S.C. 154(b) by 446 days.

(21) Appl. No.: 12/104,354

(22) Filed: Apr. 16, 2008

(65) Prior Publication Data

US 2008/0255774 A1 Oct. 16, 2008

Related U.S. Application Data

(60) Provisional application No. 60/912,112, filed on Apr. 16, 2007.

(51) Int. Cl.
*G01B 3/00* (2006.01)

(52) U.S. Cl. ......................................................... 702/33
(58) Field of Classification Search ............... 702/33–36
See application file for complete search history.

(56) References Cited

U.S. PATENT DOCUMENTS

2007/0118301 A1* 5/2007 Andarawis et al. ............. 702/33
* cited by examiner

*Primary Examiner* — Drew A Dunn
*Assistant Examiner* — Stephen Cherry
(74) *Attorney, Agent, or Firm* — Innovation Counsel LLP

(57) ABSTRACT

A method for adjusting signal data detected in a structural health monitoring (SHM) system to compensate for the effects of environmental variables acting thereon includes constructing a baseline data space comprised of sets of signal data. Current signal data sets are collected for comparison to the baseline data space. The collected current signal data sets are amended to best match baseline signal data sets in the baseline data space. A set of indices are computed for comparing the amended current signal data set to the baseline signal data sets. A threshold for detection is determined by outlier detection for the computed indices. A signal in the collected signal data set is determined to be detected on the basis of the threshold. A representation of the detected signal strength is provided on the basis of the computed indices.

15 Claims, 6 Drawing Sheets

DYNAMIC ENVIRONMENTAL CHANGE COMPENSATION OF SENSOR DATA IN STRUCTURAL HEALTH MONITORING SYSTEMS

RELATED APPLICATIONS

This application claims the benefit of U.S. provisional patent application No. 60/912,112, entitled "Structural Health Monitoring System And Methods For Use," filed Apr. 16, 2007, the entire disclosure of which is incorporated herein by reference.

TECHNICAL FIELD

This invention relates generally to the field of structural health monitoring (SHM). More specifically, this invention relates to methods for dynamically compensating data collected by a SHM system for environmental changes that affect the data.

BACKGROUND

Current state-of-the-art methodologies in structural health monitoring and damage detection rely heavily on the use of baseline data collected from the structure in the undamaged state. The methodologies are based on comparing the current sensor response signal data to the previously recorded baseline sensor response signal data, and using the differences to glean information about structural damage therefrom. It is known that environmental effects (such as temperature) can cause changes in the recorded signals, including baseline data, which in turn, will adversely affect most damage detection and evaluation schemes. However, a prior set of baseline data may not be readily obtainable, or environmental sensors may not be able to function under all operational conditions. Therefore, to overcome this difficulty, it is desirable to have a method for dynamically compensating sensor response signal data for the effects of environmental variables, such as temperature or other environmental variables, using sparse data acquired during the operation of a SHM system without the need to measure the environmental variables.

SUMMARY

In accordance with the present disclosure, techniques are provided that utilize multiple sets of data to compensate dynamically for effects caused by environmental changes that may alter the response signal data of the arrays of sensors/transducers utilized in SHM systems. A baseline set of data may be constructed dynamically and concurrently with the process of structural health monitoring damage detection obtained from the sensor array of the structure under various environmental conditions. Furthermore, the baseline data sets may be relatively sparse.

For example, data may be acquired according to one environmental effect, such as temperature, in larger increments, such as 10 to 20° C. increments, rather than, for example, 1 to 2° C. increments. Further, in appropriate cases, it may be unnecessary to obtain a measure of temperature corresponding to the acquired data signal, as other parameters (discussed below) may be used to establish the range of temperature covered. Other environmental variables may include load, strain, moisture content, pH, or any environmental condition that may cause a change in the response of a sensor, which may be typically calibrated for a given set of environmental conditions. The data sets obtained may be for sparse increments of the environmental parameter and may be dynamically added to a baseline set for each individual actuator-sensor path of the array and/or region on the structure. At a later time, when a sensor scan is performed to search for damage, the newly recorded signals are compared to the dynamically created baseline, and the effects of the environmental variable can be offset.

The method may also be used to determine a "best fit" function curve to the environmental variable, and to provide a continuous correction for all values in the variable range. Thus, reading and correcting signals transmitted between transducers along the corresponding actuator-sensor paths and/or regions on the structure, as well as the baseline data itself may provide a more accurate method of damage assessment.

In one embodiment of the disclosure, a method for compensating detected sensor signal data for the effects of environmental changes thereon includes constructing a baseline data space comprised of sets of signal data. Current signal data sets are collected for comparison to the baseline data space. The collected current signal data sets are amended to best match baseline signal data sets in the baseline data space. A set of indices are computed by comparing the amended current signal data set to the baseline signal data sets. A threshold for detection is determined on the basis of the computed indices. A signal in the collected signal data set is determined to be detected on the basis of the threshold determined. A representation of the detected signal strength is provided on the basis of the computed indices.

In another embodiment of the disclosure, a method for constructing a baseline data space includes selecting a path between two of an array of transducers mounted on a structure. A selected number of signal data sets corresponding to the selected path are collected. Electromagnetic interference (EMI) cross-talk is removed from the selected signal data sets. A Euclidean distance parameter is computed between all pairs of the collected signal data sets. The selected signal data sets are clustered in a selected number of groups according to the mutual proximity of the signal data sets as determined by the computed distance parameter. A center for each clustered group of signal data sets is defined as the location of the signal data set within the cluster group having the smallest average value of a distance parameter from all of the other members of the cluster group. All signal data sets in each respective cluster group are then discarded except the signal data set at the defined group center. Only the group center baseline signal data sets are included in the baseline data sets. The method of constructing the baseline signal data sets from the group center baseline signal data sets is repeated for all selected paths.

In another embodiment of the disclosure, a method for amending a current sensor signal data set to compensate for the effects of environmental changes thereon includes removing EMI cross-talk from the current signal data set. The current signal data set is segmented to select a time window that includes the featured components, such as the wave packet transmitted directly from an actuator to a sensor (the first arrival wave packet), of a signal in each data set. The cross correlation between a current signal data set and the selected one or more group center baseline signal data sets is computed to determine the relative time shifts of the current signal data set with respect to each of the group center baseline signal data sets. The current signal data set is then time shifted to match each of the group center baseline signal data sets. The group center baseline signal data set that has the minimum difference from the respective shifted current signal, characterized, for example, using Euclidian distance, is selected as the "best match" of the baseline signal data set to the current data signal set. This process is referred to herein as flexible matching, and will compensate the temperature effect, which is the most influential environment factor, within a certain range of temperature variation, e.g., 10 to 20° C., depending on the structural material.

In another example embodiment of the disclosure, a system for compensating detected sensor signal data for the effect of environmental changes thereon in a SHM system includes a plurality of transducers configured in an array and attached to a structure to be monitored. A computer is operably coupled to the array via an interface. The computer includes a memory for storing modules of executable instructions and data provided by the array of transducers and output from the executable modules. A display provides a presentation of information corresponding to the data compensated for the environmental effects. A processor generates signals provided to the array, receives sensor output signal data from the array, and executes the modules of instructions based on the data provided by the array. The executable modules comprise a baseline data space constructor for processing signal data prior to damage detection and a concurrent baseline constructor and damage detector for processing signal data during damage detection, wherein the damage detection is determined on the basis of the constructor and detector modules.

A better understanding of these and other features and advantages of the present invention will be more readily apparent from consideration of the detailed description of some exemplary embodiments thereof set forth below, particularly if such consideration is made in conjunction with the accompanying drawings, wherein the same or like reference numbers are used in the figures thereof to refer to the same or like elements.

DETAILED DESCRIPTION

Methods and systems are disclosed for compensating data of a structural health monitoring (SHM) system for the effects of environmental variables thereon. In one example embodiment, the method may be applied to a SHM system including an array of transducers attached to a structure to be monitored for damage. The transducers may, for example, be adapted to excite elastic waves to be transmitted along paths of the structure from one of the transducers to another one or more of the transducers for detection thereby. The data may comprise a signal waveform data set. The methods include processing the data sets, in which the value of the environmental variables are not necessarily known.

Figure 1:
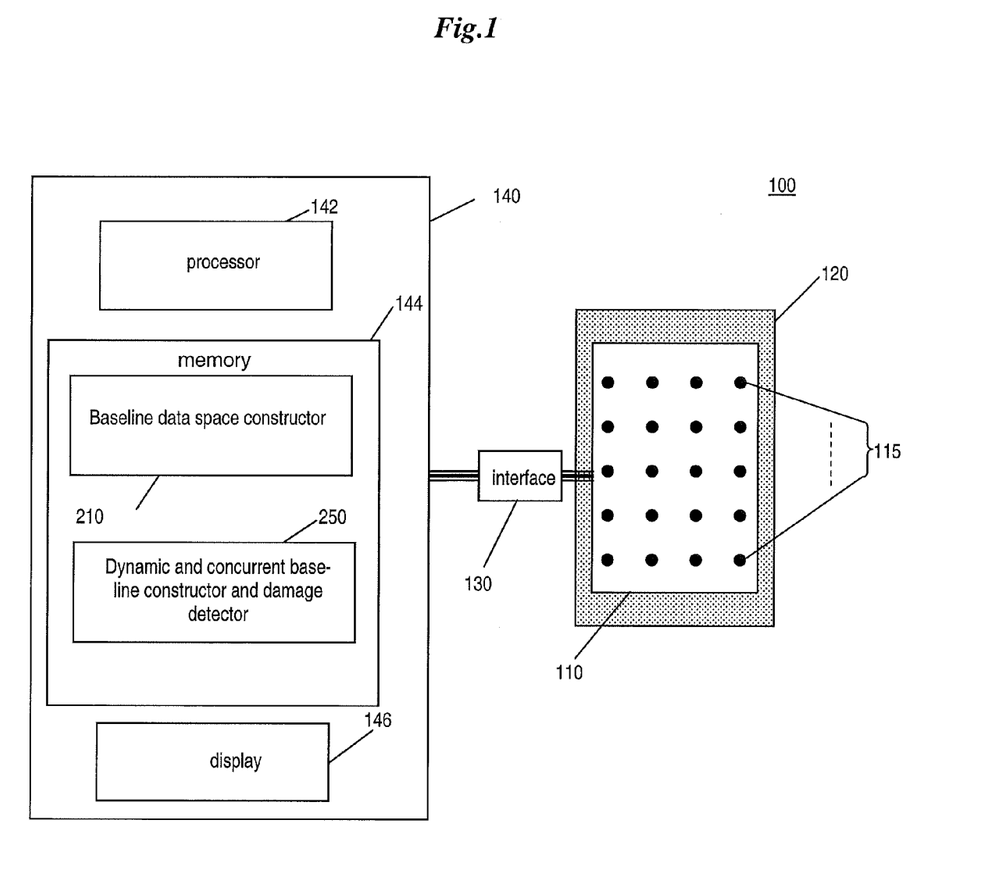
FIG. 1 is a functional block diagram of an exemplary embodiment of a system for compensating sensor signal data detected in a structural health monitoring (SHM) system for environmental effects thereon in accordance with the present disclosure.

FIG. 1 is a functional block diagram of an exemplary embodiment of a system 100 for compensating sensor signal data detected in a structural health monitoring (SHM) system for environmental effects acting thereon in accordance with the present disclosure. The system 100 comprises an array 110 of transducers 115 attached to a structure 120 to be monitored for damage. The array 110 is operably coupled to an interface 130 for communication of signals and data to and from a computer 140. The computer 140 comprises a processor 142 and a memory 144, and may further include a display 146, which may be internal or external to the computer 140. In the particular embodiment of FIG. 1, the display 146 is disposed internal to the computer 140. The processor 142 is operable to execute a plurality of executable codes, which may include a baseline data space construction module 210 and a dynamic and concurrent baseline construction and damage detection module 250, which may be stored in the memory 114, and which are described in more detail below. In addition, the memory may receive data comprising various data sets from modules 210 and 250, which are also described in more below, for the purpose of adjusting sensor signal data to compensate for environmental effects thereon and for detecting damage in the structure 120. The display 146 or other equivalent output means (not illustrated) may be provided for presentation of damage detection information at various stages of the data adjustment.

In one embodiment, the transducers 115 may be piezoelectric actuator/sensors, e.g., lead-zirconate-titanate (PZT) transducers, capable of both exciting and detecting elastic waves which propagate through paths in the structure 120 from one transducer in the array to another. Transducers 115 may be operated in a pulsed mode, i.e., a mode wherein a short burst of an electrical excitation signal applied thereto produces a resonant elastic response that is coupled into the structure. Elastic waves then propagate uniformly in all directions in the structure, or alternatively, the transducer 115 may be configured to propagate elastic waves in preferred directions therein. For example, where damage or defects in the structure manifest as cracks opening to the surface of the structure 120, the elastic waves generated are preferably surface elastic waves that propagate in all directions on the surface, and are therefore detectable by a plurality of transducers 115 of array 110. Other configurations of the array 110 may also be implemented, for example, where elastic waves are transmitted from a portion of the array 110 through an interior volume of the structure 120 and detected by the transducers 115 in another portion of the array 110, thereby detecting latent or embedded flaws.

Figure 2:
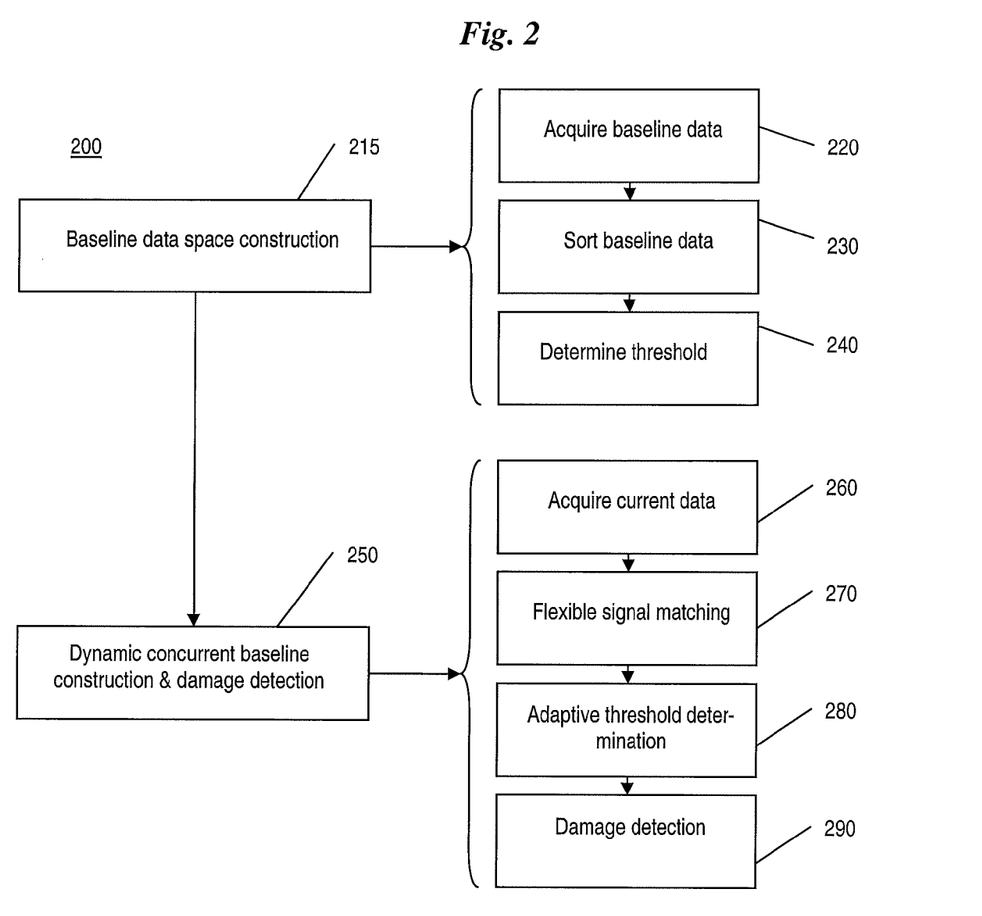
FIG. 2 is a process flow diagram of an exemplary embodiment of a method for compensating SHM system sensor signal data for environmental effects in accordance with the present disclosure.

In FIG. 2, an exemplary method 200 for compensating sensor signal data for environmental effects includes constructing (step 215) a baseline data space using the module 210. Baseline data space construction 215 may include several processes, such as, for example, acquisition of baseline data (step 220), sorting the baseline data into groups (step 230) to reduce the quantity of baseline data required, and computing threshold values (step 240) for determining in subsequent steps when new or current data contains a signal indicating the presence of an outlier that may, for example, represent damage in the structure.

In one embodiment, the baseline data space may represent data accumulated prior to operating a SHM system to test for damage in the structure. Having established a baseline data space for the undamaged structure using the baseline data space construction (step 215), a dynamic process of concurrently updating the baseline data space and detecting damage (step 250) may comprise several steps, including, for example, acquiring current data (step 260), amending the data to determine a best match with data in the baseline data space, referred to herein as "flexible signal matching" (step 270), adaptively determining thresholds for deciding if an amended data set contains a signal indicative of damage (step 280), and determining if the signal represents damage or a transient effect caused by a change in one or more environmental variables (step 290).

Figure 3:
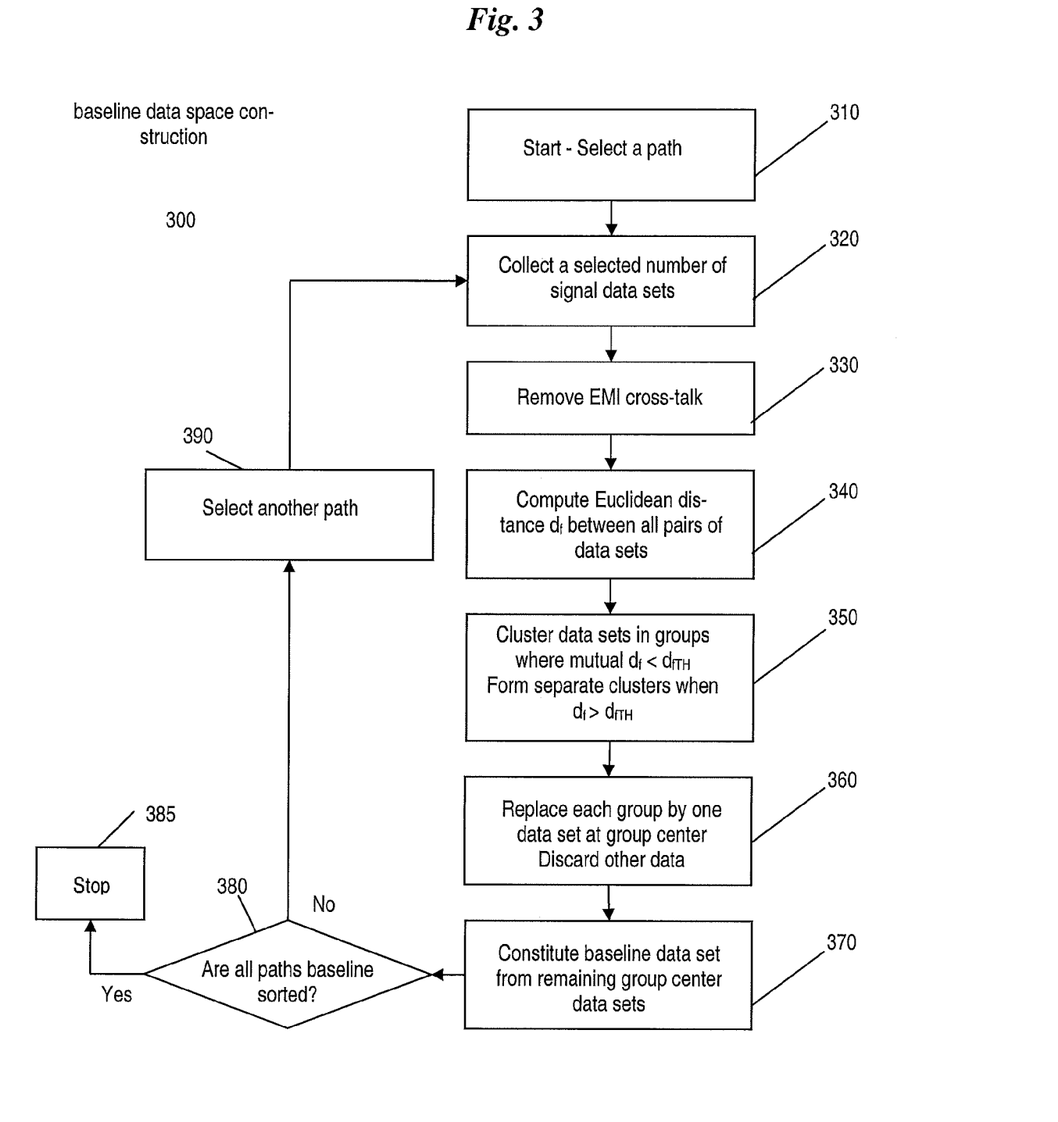
FIG. 3 is a process flow diagram of an exemplary embodiment of a method for baseline data space construction in accordance with the present disclosure.

The baseline data space may comprise the sorted sets of waveforms obtained for the selected paths, as described below. FIG. 3 illustrates an exemplary embodiment of a method 300 for constructing a baseline data space for each of the plurality of selected paths. A plurality of signal data sets may be collected over time (step 320), under the assumption that a range of different values of environmental effects on the signal data may occur when the signal data is acquired. This may not in fact be the case, so that continued baseline data acquisition and sorting may take place while damage detection data is also being acquired, as discussed below. The value of the environmental variable(s) affecting the data may not be measurable, and therefore may not be known.

For each signal detected, there may be electromagnetic interference (EMI) cross-talk present thereon, which is preferably removed (step 330). This may be done, for example, by replacing with zeros all data values in a first portion of the waveform received by a second transducer that correspond to the time length of the signal excited at a first transducer in a path which is detected by direct radiation transmission at the second transducer. That is, direct electromagnetic transmission of the signal may arrive before the elastic wave signal, and may be cancelled out of the received waveform. Of course, other methods, such as time gating to ignore the period of direct transmission, may also be employed.

For the selected path, a method is required for identifying differences between the signal data sets that may be the result of environmental changes. For example, a Euclidean distance $d_f$ may be computed (step 340) between all pairs of data sets. Changes in environmental variables may cause considerable changes to the signal data. However, to a certain extent, the type of signal data changes caused by changes in environmental variables can be different from that caused by structural damage. For example, within certain temperature variation ranges (e.g., variations of up to 10-20° C., depending on the material of the structure), the signal change caused by temperature variation has the following basic characteristics: (1) the signal change is mainly a change in phase, i.e., a shift in the signal waveform in time delay due to a velocity dependence on temperature, and (2) the amplitude does not change significantly.

Each signal datum may be considered as a vector array. For example, each data point in a data signal may have a time and amplitude, defining two vector coordinates. The Euclidean distance between two signal vectors, denoted by $d_f$, is the "distance" between the two signal vectors. $d_f$ is a scalar quantity. As an example of calculating $d_f$, consider a data segment to have N data points. Thus, $X0(j)$ is composed of $X0^j = \{X0^j_1, X0^j_n, \ldots X0^j_N\}$ for the $j^{th}$ baseline data set, and similarly for the $i^{th}$ baseline data set. $d_f^{i,j}$ may then be calculated (in step 340) as a Euclidean distance, for example, by $$d_f^{i,j} = \sqrt{\sum_{n=1}^{N} (X0^i_n - X0^j_n)^2},$$

where, if i=j, (i.e., the $i^{th}$ and $j^{th}$ baseline data sets are identically themselves) the overlap is perfect, and the distance of the vector from itself is zero.

The values of $d_f^{i,j}$ may be clustered (step 350) into different groups. For example, in each group, the values of $d_f^{i,j}$ may be less than a certain "distance," i.e., the baseline data set vectors are located in proximity to each other by less than a certain selected threshold distance $d_{fTH}$, which may be selected to identify the group. Conversely, some data sets will be located farther away, i.e., at a distance greater than $d_{fTH}$, but may themselves be located in proximity to each other by less than $d_{fTH}$. In this manner, the signal data sets may be sorted and a plurality of groups may be determined.

For each group, a "group center" may be determined (step 360) as the data set having the smallest average distance, e.g., $\langle d_f \rangle$, from all of the other members of the group. All other signal data sets in the group may then be discarded, and the signal data set at the group center retained (step 370) as a single member constituting (step 370) the baseline data space for the selected path. Similarly, all other groups obtained are replaced by the respective group center signal data set. This sorting and clustering process reduces the amount of data that is retained for use in later steps for adjusting the data to compensate for environmental effects.

The set of signal data sets obtained as above represents the portion of the baseline data space corresponding to a selected path. If there are selected paths for which the data acquisition, clustering and sorting has not been done (a "No" result in decision step 380), then method 300 continues by selecting another path (step 390) and repeating the steps of steps 320-370. The process may be repeated for all selected paths between transducers on the structure to establish the baseline data space for the structure, and terminates (step 385) when a "Yes" result in decision step 380 is obtained.

A detection threshold may be determined in terms of the baseline data space signal data sets for each selected path by examining differences in baseline signal data sets which may be due to differences caused by environmental effects. In an exemplary method, let $X0^r$ be a group center signal data set selected as a reference with respect to the other group center signal data sets $X0^j$. A set of baseline indices may then be calculated for each such group center signal data set from the following relationship:

$$I_{BL}(j) = \frac{\sqrt{\sum_{m=1}^{M} (X0(j)_m - X0(1)_m)^2}}{\sqrt{\sum_{m=1}^{M} (X0(j)_m^2 + X0(1)_m^2)}},$$

where $I_{BL}(j=1)=0$. All baseline index values $I_{BL}(j)$ for j other than j=1 may be expected to have positive non-zero values. One of these may be selected as a threshold value $I_{TH}$ that serves as a basis for determining whether a signal indicates the presence of, for example, damage to the structure, as described below. The choice of index may be user specified, and may correspond to the nearest "neighbor," i.e., the group center signal data set that is closest to the reference data set.

Alternatively, a threshold index value may be selected by choosing a group center signal data set that is farther away in Euclidean space.

Figure 4:
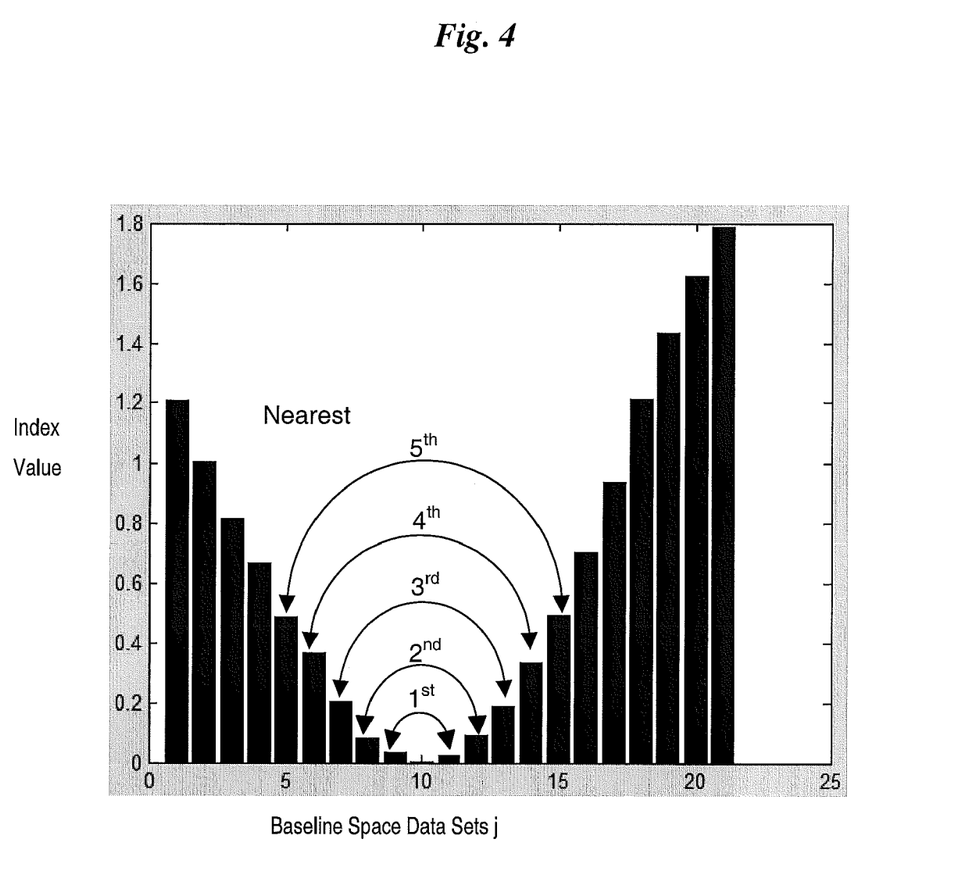
FIG. 4 is a chart illustrating exemplary index values obtained for a selected path in a SHM system according to an embodiment of the present disclosure.

FIG. 4 is a chart illustrating exemplary index values obtained for a selected path in a SHM system according to an embodiment of the present disclosure, wherein baseline group center signal data set #10 has been chosen as the reference. It may be appreciated, as discussed below, that selecting as a threshold index $I_{TH}$, for example, the $5^{th}$ nearest neighbor will be less sensitive in detecting a damage signal than selecting the $1^{st}$ nearest neighbor. Conversely, selecting the first nearest neighbor may result in a noisy signal being incorrectly recognized as an indication of damage. In a like manner, a threshold may be selected for each of the selected paths on the structure.

Construction of the baseline data space may be accomplished dynamically and concurrently with the process of damage detection, as indicated in FIG. 2, step 250. As discussed above in connection with FIG. 2, a method 250 of dynamic concurrent baseline construction and damage detection may include, for a selected a signal path, acquiring current data (step 260), a method of flexible signal matching (step 270), wherein the current data is adjusted and a best fit is found with one of the group center baseline signal data sets, and determining an adaptive threshold (step 280), based on outlier detection and whether an event that generates a current data signal represents a transient (e.g., environmental) event, or is an indication of a permanent event, such as damage. Damage may then be determined (step 290), as described below.

Figure 5:
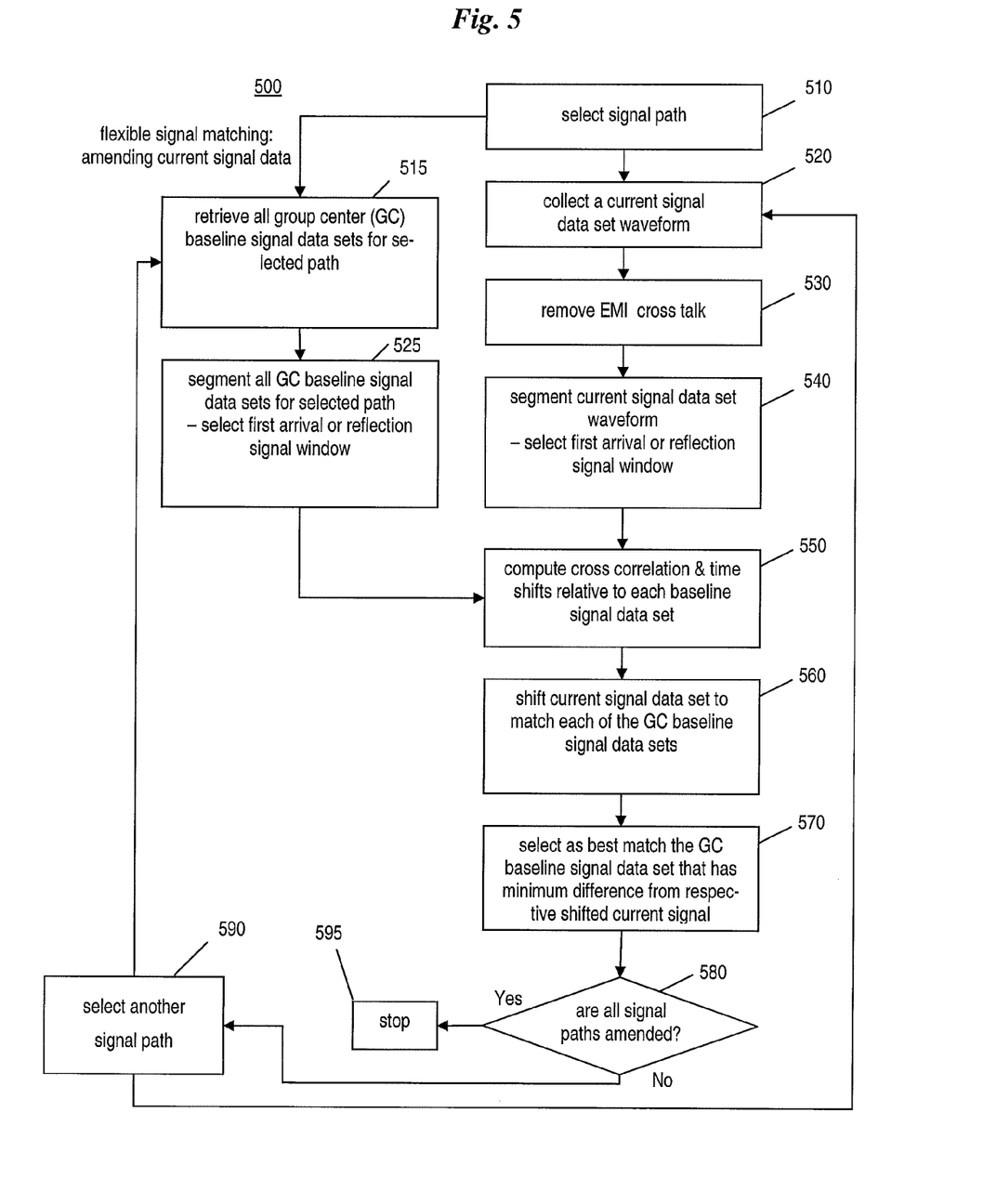
FIG. 5 is a process flow diagram of an exemplary embodiment of a method for flexible signal matching in accordance with the present disclosure.

FIG. 5 illustrates an example embodiment of a method 500 of flexible signal matching that includes selecting a signal path (step 510) and retrieving (step 515) the baseline signal data sets consisting of the group center baseline data sets constituted for the selected path in accordance with the baseline data space construction method 300. A current signal data set waveform is collected (step 520) for the selected path and the EMI cross-talk is removed therefrom (step 530). The resulting current data set is segmented (step 540) to provide separate time windows that select a first arrival signal and/or a reflection signal. The segmented window selected for the following steps depends on the use chosen for the data in subsequent procedures. Concurrently with the segmentation of the current signal data set (in step 540), each of the plurality of baseline signal data sets are similarly segmented (step 545) for a first arrival signal.

The segmented current signal data set is cross correlated (step 550) with each of the plurality of segmented baseline signal data sets to obtain a time shift of the current data signal relative to each of the baseline signal data sets. The current signal data set is then time shifted (step 560) to match each of the baseline signal data sets. The baseline signal data set that has the minimum difference from the respective shifted current signal data set is selected (step 570) as the best match baseline signal data set. It may be noted that the shifting, in effect, removes, or "de-trends," the temperature effects to a certain extent on the data locally.

If there are more signal paths to be matched, (a No result in decision step 580), another signal path is selected (step 590), the corresponding baseline signal data set retrieved (step 515) and a current signal data set is collected (step 520), and the flexible signal matching process is then repeated. If all signal paths have been matched (a Yes result in decision step 580), method 500 terminates, and method 200 continues with adaptive threshold determination 200 (FIG. 2).

Figure 6:
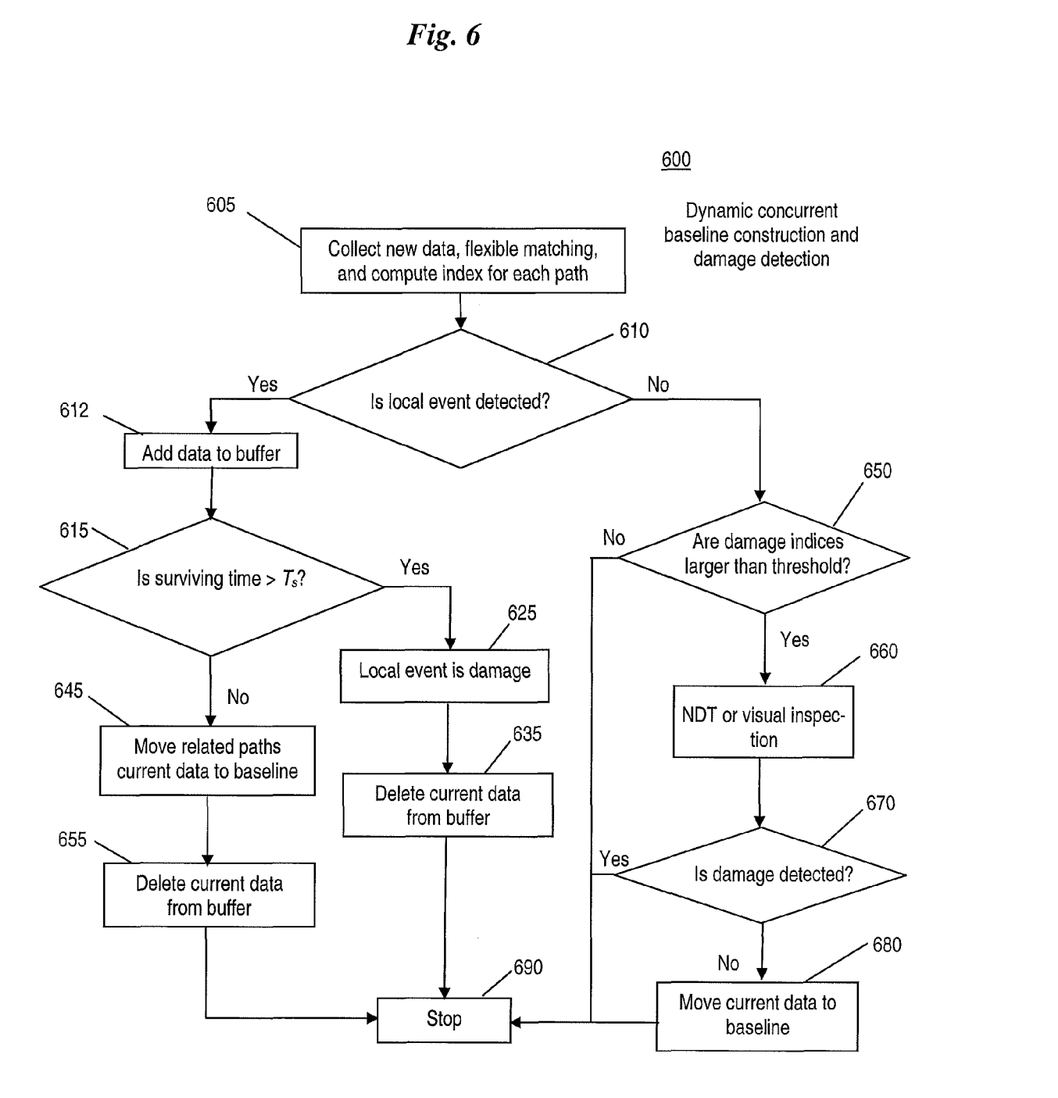
FIG. 6 is a process flow diagram of an exemplary embodiment of a method for dynamic concurrent baseline data space construction and damage detection in accordance with the present disclosure.

As illustrated in FIG. 6, in an embodiment of a method 600 for dynamic concurrent baseline data space construction and damage detection, new (i.e., "current") data is acquired (step 605) for each of the actuator-sensor paths. The data is processed with the above-described flexible matching and a best match damage index is computed, for example, by:

$$I(k) = \frac{\sqrt{\sum_{m=1}^{M}(X(k)_m - Y(k)_m)^2}}{\sqrt{\sum_{m=1}^{M}(X(k)_m^2 + Y(k)_m^2)}}$$

where X(k) denotes the shifted new data of the $k^{th}$ path and Y(k) denotes the corresponding best match baseline data of the $k^{th}$ path (step 605). I(k) represents the normalized difference between the best match baseline signal data set and the shifted new data of the $k^{th}$ path.

The baseline data space construction and damage detection may take advantage of the condition that, in most cases, damage is initially a local spatial event, i.e., only signals of direct-passing and neighboring paths of a damage are changed, and the change is monotonic, i.e., it is not transient and does not disappear over time. Furthermore, a signal change caused by variation in environmental parameters tends to be characterized by a finite survival time, i.e., it is transient. To distinguish between transient environmental effects and local damage-like events, a "baseline" and a "baseline buffer" may be created. Depending on conditions described later, a current signal data set may or may not be moved from the baseline buffer to the baseline.

To detect a local spatial event, a statistical outlier detection method, for example, the Grubbs test described in F. E. Grubbs, "Procedures for Detecting Outlying Observations in Samples," Technometrics, 1-21, Vol. 11 (1969), incorporated herein by reference, may be used. In the present application, the Grubbs test computes a measure of the difference between the mean value of, for example, all the best match damage indices corresponding to the paths on the structure and the value at a particular location, normalized by the standard deviation of damage indices. The index that produces the largest value of the Grubbs test calculation may be considered an outlier, and may serve as an indication of damage. The test for localized damage may be repeated for the best match damage indices at all other locations. The threshold value of the Grubbs Test may serve as a determinant for the detection of damage. The Grubbs Test calculation is given by the relationship $$z(k) = \frac{<I> - I(k)}{\sigma},$$

where z(k) is the Grubbs test value of the $k^{th}$ best match index I(k) corresponding to the $k^{th}$ selected path, and <I> and σ are the mean and standard deviation of all best match indices corresponding to the selected paths. A threshold value $z_{TH}$ derived on the basis of <I> and σ may be used to determine that a local spatial event is detected for the $k^{th}$ selected path if z(k) is greater than $z_{TH}$, i.e., if z(k) is an outlier. Plotting the values of the Grubbs Test outliers corresponding to the selected path locations is an exemplary way to identify and display the damage.

If the new data shows a local spatial event detected based on the existing baseline (a Yes result in decision step 610) using outlier detection, and is therefore suspected of being indicative of structural damage, this data may be temporarily added to a "baseline buffer" (step 612). Suppose $T_s$ is a specified threshold time constant for the survival of a spatially local event. The survival time of a local event, i.e., a time constant representative of the persistence of the current signal data over time, may be compared to $T_s$ (step 615). If the measured time is greater than $T_s$ (a Yes result in decision step 615), the local event may be treated as a damage (step 625), and the current data may be deleted from the baseline buffer (step 635).

If, however, the measured persistence time t is less than $T_s$ (a No result in decision step 615), the local event may be treated as an environmental disturbance (i.e., as transient), the current data for the local event related paths, i.e., the outlier paths, may be moved to the baseline (step 645). Since the signal has been accounted for, the current data may be deleted from the baseline buffer (step 655). The baseline now contains data representative of the local environmental disturbance by virtue of the index calculated. At some later time, clustering and sorting procedures may condense this data set into a "dynamically updated" group center baseline data set.

If no spatially local event is detected (a No result in decision step 610), the best matching damage indices may be compared with a threshold (step 650). In the case where the indices are smaller than the threshold (a No result in decision step 650), the structure is considered as in a healthy condition.

In the case where the indices are larger than the threshold (a Yes result in decision step 650), the current baseline may not be sufficient to determine whether there exists a local spatial event in the current data. Other techniques, e.g., NDT or visual inspection, may be employed to confirm the structure condition (step 660). If the inspection shows that a damage does not exist (a Yes result in decision step 670), the current data may be added to the baseline. Again, at some later time, clustering and sorting procedures may condense this data set into a dynamically updated group center baseline data set. By continuingly adding new data of different environment conditions to the baseline, the capability of the baseline in detecting local events will be increasingly enhanced, and it will be less needed to employ NDT or visual inspection.

Having thus described exemplary embodiments of the present disclosure, persons of ordinary skill in the art will recognize that changes may be made in form and detail without departing from the scope of the invention. For example, whereas, the embodiments previously described have been in the context of temperature as the changing environmental variable, other environmental variables may be compensated for, such as moisture content in a graphite/epoxy structure, wind forces, changing compressive or tensile loads (either hydrostatic or tensor). Other environmental factors may also be compensated for without limiting the scope of the invention, which is commensurate with that the following claims and their functional equivalents.

What is claimed is:

1. A method for adjusting sensor signal data detected in a structural health monitoring (SHM) system to compensate for the effects of an environmental variable acting on the data, the method comprising:
    detecting one or more sets of a sensor signal data from an array of transducers mounted on a structure being monitored by the SHM system;
    constructing a baseline data space comprising the one or more sets of the sensor signal data detected;
    detecting one or more current sets of the sensor signal data from the transducers at a later time at which the environmental variable is acting to affect the data;
    amending the baseline data space with the current sensor signal data sets while they are being detected; and,
    determining if the current sensor signal exceeds a selected threshold value on the basis of the amended baseline data space; and
    repeating the detecting one or more current sets of the sensor signal data, the amending, and the determining for each of a plurality of signal propagation paths in the structure respectively extending between associated pairs of the transducers.

2. The method of claim 1, wherein the constructing of the baseline data space comprises:
    selecting a propagation path;
    collecting a selected number of sensor signal data sets corresponding to the selected path; and,
    repeating the preceding steps for each of the propagation paths of the structure.

3. The method of claim 2, wherein the constructing of the baseline data space further comprises removing electromagnetic interference (EMI) cross-talk from each of the sensor signal data sets detected.

4. The method of claim 3, wherein the constructing of the baseline data space further comprises:
    computing a Euclidean distance parameter between all pairs of the signal data sets for the selected path; and,
    selecting a distance parameter from among the computed distance parameters as a threshold distance parameter $d_{fTH}$.

5. The method of claim 4, wherein the constructing of the baseline data space further comprises sorting the sensor signal data, wherein the sorting of the signal data comprises:
    clustering the signal data sets in a selected number of groups according to a mutual proximity of the signal data sets as determined by the computed distance parameter; and,
    defining a center for each clustered group of signal data sets as the location of a signal data set within the cluster group having the smallest average value of distance parameter to all other members of that cluster group.

6. The method of claim 5, further comprising:
    discarding all signal data sets in each respective cluster group except the signal data set at the defined group center; and,
    including in each of the baseline signal data sets only the respective group center baseline signal data set thereof.

7. The method of claim 6, further comprising forming the baseline data space from the plurality of baseline data sets.

8. The method of claim 7, further comprising determining the value of the signal detection threshold for each propagation path.

9. The method of claim 8 wherein the determining of the threshold value comprises:
    selecting a first baseline signal data set from among the group center baseline signal data sets;
    calculating a clustered baseline data index $I_{BL}(j)$ for all baseline signal data sets relative to the first baseline signal data set for the selected path from the relationship:

$$I_{BL}(j) = \frac{\sqrt{\sum_{m=1}^{M}(X0(j)_m - X0(1)_m)^2}}{\sqrt{\sum_{m=1}^{M}(X0(j)_m^2 - X0(1)_m^2)^2}},$$

wherein $I_{BL}(j)$ is the index of the jth clustered baseline signal data set $X0(j)$ of the selected path relative to the selected first baseline signal data set, and wherein j=1 corresponds to the selected first group center baseline signal data set; and, selecting as a threshold an index value $I_{BL}(j)$, where j is other than j=1.

10. The method of claim 4, wherein the computing of the Euclidean distance parameter pairs of signal data sets for all pairs of baseline signal data sets for the selected path comprises:

calculating the distance parameter $d^{i,j}_f$ from the relationship:

$$d^{i,j}_f = \sqrt{\sum_{n=1}^{N} (X0^i_n - X0^j_n)^2},$$

where $X0^i_n$ and $X0^j_n$ are the nth data point values of N data points contained in the $i^{th}$ and $j^{th}$ baseline data sets of $X0^i$ and $X0^j$, respectively.

11. The method of claim 1, wherein the amending of the baseline data space comprises:
   detecting a current sensor signal data set for a selected propagation path of the structure;
   holding the current signal data set in a baseline buffer;
   matching the current data set to a best baseline signal data set;
   specifying a threshold value for the detection of a signal based on the best match baseline data set; and,
   determining whether the current data set represents a detection of a local event comprising either an environmental effect or a damage of the structure on the basis of the threshold value specified.

12. The method of claim 11, wherein the matching of the current signal data set to a best baseline signal data set comprises:
   removing electromagnetic interference (EMI) cross-talk from the current signal data set;
   retrieving the plurality of baseline signal data sets for the selected path;
   segmenting the current signal data set and the plurality of baseline signal data sets to select a first arrival signal;
   computing a cross correlation between the current data set and each of the plurality of baseline signal data sets;
   obtaining a time shift for each of the cross correlation computations corresponding to each of the plurality of baseline signal data sets;
   selecting the baseline signal data set that has the minimum difference to the respective shifted current signal as the best match baseline; and,
   shifting the current signal data set waveform by the time shift corresponding the to best match baseline data set.

13. The method of claim 11, further comprising:
   detecting the local spatial event using outlier detection techniques;
   specifying a survival time $T_s$ corresponding to the detected local event;
   measuring the persistence of the local event;
   determining that the local event is damage if the persistence time is greater than $T_s$; and,
   determining that the local event is an environmental effect if the persistence time is less than $T_s$.

14. The method of claim 13, wherein the detecting of the local spatial event using outlier detection techniques comprises:
   computing an index of the shifted current data set relative to the best match baseline date for each of the plurality of selected paths;
   computing a mean value and a standard deviation from the plurality of best match damage indices;
   computing a Grubbs test value z(k) for each best match damage index from the relationship:

$$z(k) = \frac{<I> - I(k)}{\sigma},$$

wherein z(k) is the Grubbs test value of the $k^{th}$ best match index I(k) corresponding to the kth selected path, and <I> and .sigma. are the mean and standard deviation of all best match indices corresponding to the k selected paths;
   determining that a local spatial event is detected for the kth selected path if z(k) is greater than the threshold of the Grubbs test.

15. The method of claim 13, further comprising:
   adding the current data of the local event-related paths to the baseline data space if the persistence time is less than $T_s$;
   deleting the current data from the baseline buffer if the persistence time is less than $T_s$;
   deleting the current data from the baseline buffer if the persistence time is greater than $T_s$;
   determining whether the damage indices are larger than a selected threshold;
   determining whether actual damage has been detected using non-destructive testing (NDT) techniques or by visual inspection; and,
   updating the baseline data set with the current data if actual damage has not been detected.

* * * * *